(12) United States Patent
Whiting

(10) Patent No.: US 6,945,965 B2
(45) Date of Patent: Sep. 20, 2005

(54) REMOTE CONTROLLED URINARY LEG/BED BAG DRAIN VALVE

(76) Inventor: Howard Anthony Whiting, 28 12 NW. 3rd Way, Battle Ground, WA (US) 98604

( * ) Notice: Subject to any disclaimer, the term of this patent is extended or adjusted under 35 U.S.C. 154(b) by 0 days.

(21) Appl. No.: 10/147,244

(22) Filed: May 16, 2002

(65) Prior Publication Data

US 2002/0173758 A1 Nov. 21, 2002

Related U.S. Application Data

(60) Provisional application No. 60/291,038, filed on May 16, 2001.

(51) Int. Cl.[7] ................................................ A61F 5/44
(52) U.S. Cl. ...................................................... 604/323
(58) Field of Search ................................ 604/323, 250, 604/34, 890, 890.1, 95.01, 95.04, 540, 544, 335; 137/247–254; 251/129.04; 128/DIG. 25

(56) References Cited

U.S. PATENT DOCUMENTS

| | | | | |
|---|---|---|---|---|
| 4,343,316 A | * | 8/1982 | Jespersen ..................... 600/584 |
| 5,074,317 A | * | 12/1991 | Bondell et al. ............. 128/886 |
| 5,201,670 A | * | 4/1993 | Watanabe et al. ........... 439/372 |
| 5,427,350 A | * | 6/1995 | Rinkewich ............... 251/30.01 |
| 5,634,778 A | * | 6/1997 | Liegel et al. ............... 417/313 |
| 5,813,655 A | * | 9/1998 | Pinchott et al. ........ 251/129.04 |
| 5,999,087 A | * | 12/1999 | Gunton ..................... 340/309.5 |
| 6,305,663 B1 | * | 10/2001 | Miller .................... 251/129.04 |
| 6,453,907 B1 | * | 9/2002 | Forsell ........................ 128/899 |
| 6,666,431 B2 | * | 12/2003 | McCusker ............. 251/129.15 |
| 6,685,159 B1 | * | 2/2004 | Schnell .......................... 251/59 |
| 6,723,086 B2 | * | 4/2004 | Bassuk et al. ........... 604/890.1 |
| 2002/0019709 A1 | * | 2/2002 | Segal .......................... 702/45 |
| 2002/0139419 A1 | * | 10/2002 | Flinchbaugh ............... 137/557 |
| 2003/0060893 A1 | * | 3/2003 | Forsell ..................... 623/23.65 |
| 2003/0097092 A1 | * | 5/2003 | Flaherty ...................... 604/67 |
| 2003/0105385 A1 | * | 6/2003 | Forsell ......................... 600/29 |
| 2003/0129944 A1 | * | 7/2003 | Chang et al. ................. 455/41 |
| 2003/0144575 A1 | * | 7/2003 | Forsell ......................... 600/29 |
| 2003/0144648 A1 | * | 7/2003 | Forsell ....................... 604/544 |

FOREIGN PATENT DOCUMENTS

| | | | | |
|---|---|---|---|---|
| CA | 2269483 | * | 10/2000 | .......... G01F/23/00 |
| EP | 0 710 490 A2 | * | 8/1996 | .......... A61M/25/10 |
| GB | 2 362 907 | * | 12/2001 | .......... E21B/34/06 |
| KR | 2001025424 A | * | 4/2001 | .......... F16K/37/00 |

* cited by examiner

*Primary Examiner*—Larry I. Schwartz
*Assistant Examiner*—Michael G. Bogart

(57) ABSTRACT

An apparatus designed to empty a urinary drain bag having a battery powered wireless remote transmitter that activates a wireless remote controlled receiv r relay connected to a battery powered solenoid operated pinch valve that is attached to a flexible drain tube, attached to an outlet of a urine drain bag to an "on" position, allowing the bag to drain for a designated period of time after which time the solenoid returns to a closed or "off" position, stopping the draining of the bag.

1 Claim, 2 Drawing Sheets

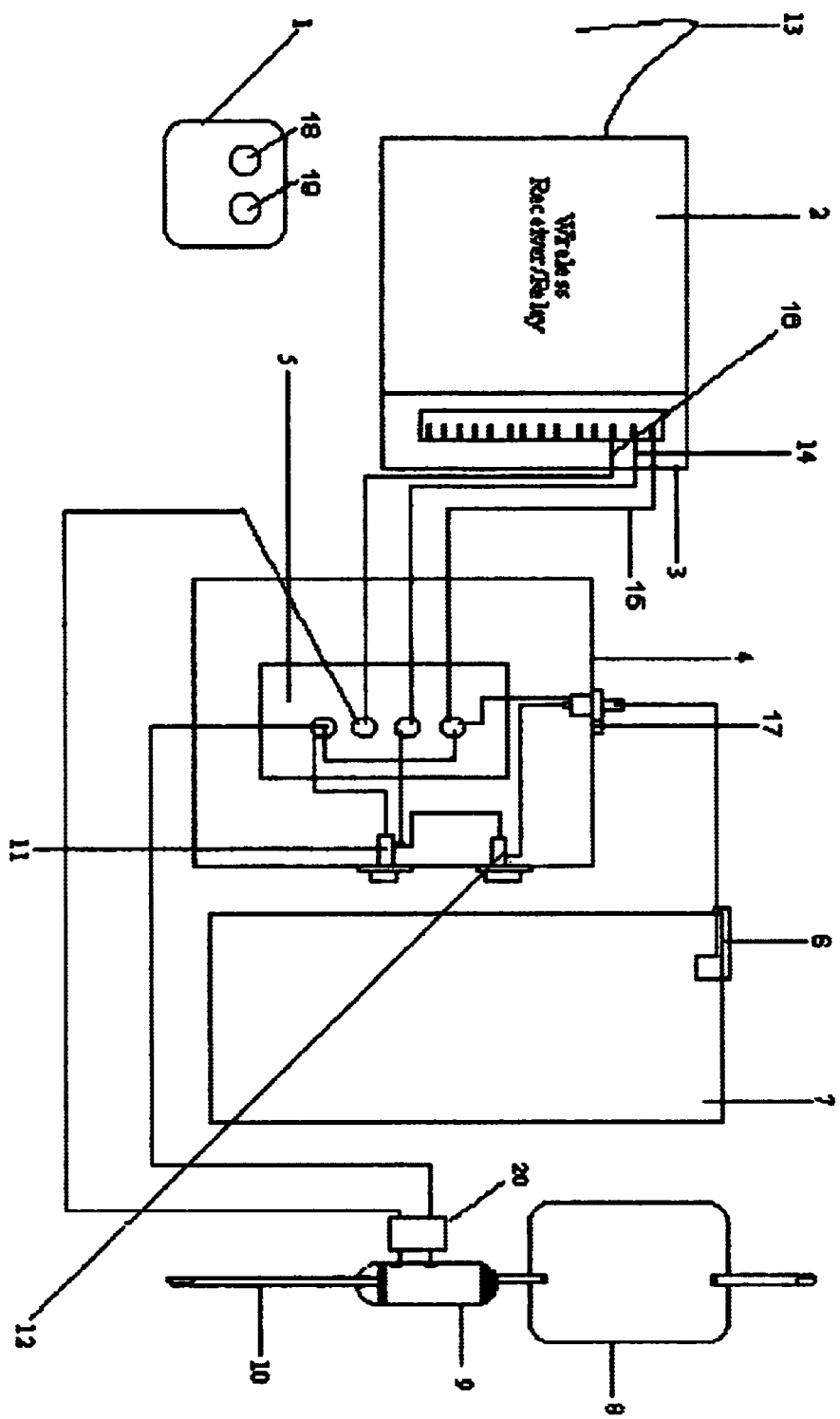

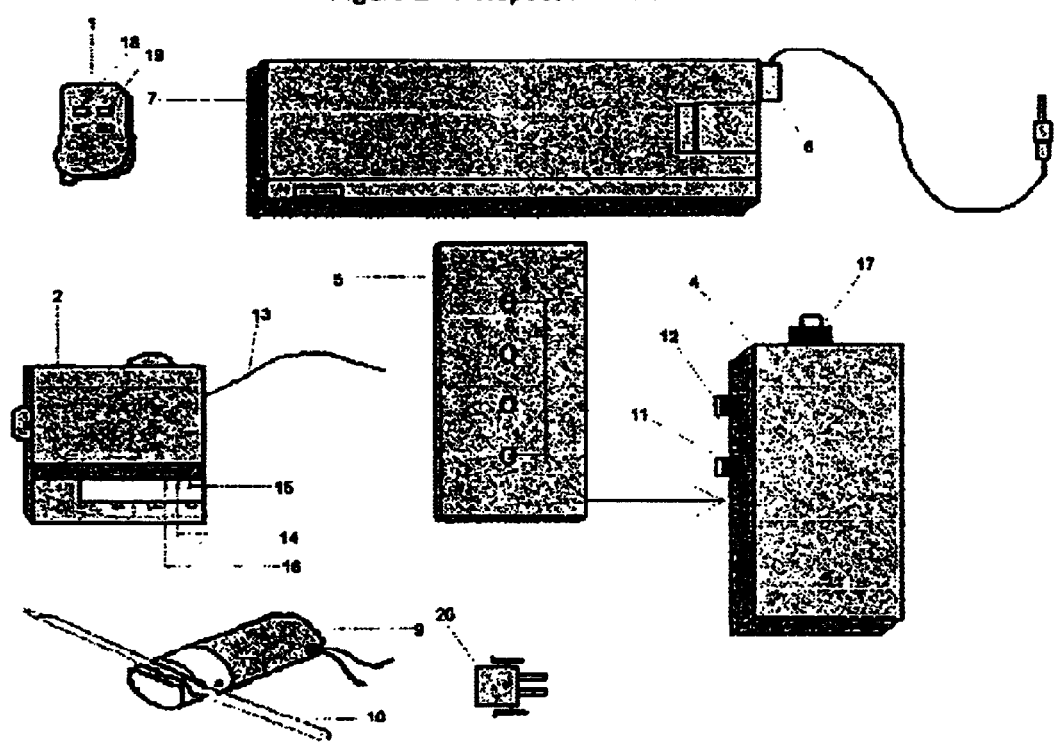

REMOTE CONTROLLED URINARY LEG/BED BAG DRAIN VALVE

CROSS REFERENCE TO RELATED APPLICATIONS

This is a continuation of Ser. No. 60/291,038, filed on May 16, 2001.

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of medical and more specifically to an apparatus to empty urinary drain bags using wireless remote control technology. Historically, wearers of urinary leg bags were often confined, usually to a wheelchair or bed, limited in mobility and dependent on an attendant to assist them in emptying their bags, causing lack of proper fluid intake resulting in ill health effects and physical discomfort. Typical emptying mechanisms were manually operated by the user or by an attendant, or a hard-wired mechanism only usable in a stationary location, restricting user mobility.

PRIOR TECHNOLOGY

The most widely used drain bag emptying device includes a common clip attached to a flexible drain tube that is unclipped to an opened position to drain the bag through the tube and then clipped to a closed position to stop the draining. This operation often requires bending and stretching by users, thus limiting users that are unable to bend or stretch or otherwise perform this task to rely on an attendant to perform the task for them. Another available mechanism uses a switch that is hard wired to battery, usually a wheelchair motor battery. The switch is also hardwired to a solenoid operated pinch valve that is worn by the user. Upon activating the switch, the solenoid pinch valve releases to an open or on position draining the bag and is returned to its closed position when switched off. Because the switch is hard wired to the battery, the user must be disconnected from the mechanism when the user moves to another location such as a bed, car, boat or push wheelchair. This limits the operation of the mechanism to its fixed location, severely impairing the mobility of the user.

Another mechanism uses pressure sensor and timing technology for the purposes of bladder recycling or for other medical use.

DEFICIENCY OF PRIOR TECHNOLOGY

The prior technology is deficient in that the mechanism uses pressure sensor and timer technology for the purpose of bladder recycling.

The prior technology is deficient for leg bag emptying application because it is pressure sensitive and/or on a timer, thus causing inconvenient emptying of bag, limiting users mobility and control (Flinchbaugh publication date Oct. 3, 2002, #US 2002/0139419-A1).

The invention does not control or affect bladder recycling, but provides an external means for emptying a leg bag of urinary content via a flexible tube using remote controlled technology. The invention is operated and controlled by the wearer or by an attendant that can operate the mechanism from a distance. There is no pressure sensor or preset timing or other automatic function to engage its operation. Further, the invention is portable and can be worn inconspicuously by the wearer for ease of mobility and aesthetics.

Further, hard-wired mechanisms limit the mobility of the user to the location where the mechanism is mounted, usually to a wheelchair motor battery, limiting its operation only from the wheelchair or a fixed location. These mechanisms are often cumbersome.

BRIEF SUMMARY OF THE INVENTION

The primary object of the invention is to provide a practical and convenient means to empty a urinary drain bag that allows more freedom of movement, ease of operation, and portability encouraging more fluids to be consumed, therefore increasing good health, comfort and quality of life.

A further object of the invention is to provide mobility for the user by providing a portable and compact apparatus worn by the user, allowing the user to move from a wheelchair to a vehicle, boat or other location and to continue to operate the apparatus from any location.

Another object of the invention is to provide through the use of wireless remote control technology the means of operation to be self operated at a distance by an attendant.

Another object of the invention is to provide a small and compact battery operated system.

A further object of the invention utilizers a battery eliminator that plugs into a typical receptacle to provide power to the mechanism when adapted to a stationary use.

A further object of the invention is to provide the ability for the battery to be charged in most vehicles or a standard electrical outlet.

Another object of the invention is to prevent accidental operation of device causing unwanted discharge from leg bag. The transmitter button must be pressed continuously for a few seconds to engage operation of solenoid to drain the leg bag.

Another object of the invention is to provide the option for the device to be mounted in any suitable location or to be worn in a discreet manner.

Other objects and advantages of the present invention will become apparent from the following description, taken in connection with the accompanying drawings, wherein, by way of illustration and example, an embodiment of the present invention is disclosed.

In accordance with a preferred embodiment of the invention, there is disclosed an apparatus to empty urinary drain bags using wireless remote control technology comprising: a solenoid operated pinch valve, connector, remote transmitter, receiver relay, circuit board, rechargeable battery, battery charger connector, battery eliminator, necessary wiring, and flexible tube.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 1 is a plan view of the invention.

FIG. 2 is a perspective view of the apparatus.

ELEMENTS OF FIG. 1

1. Wireless transmitter—remote mounted or hand-held
2. Wireless receiver/relay
3. Terminal strip
4. Case
5. Terminal strip
6. Battery clip
7. Rechargeable battery
8. Urinary leg bag
9. Solenoid pinch valve (normally closed)
10. Flex drain tube
11. Battery charger connection
12. Fuse
13. Antenna
14. DC
15. DC
16. DC
17. Battery connector
18. On transmitter
19. Off transmitter
20. Connector
21. Tube from catheter

DETAILED DESCRIPTION OF THE PREFERRED EMBODIMENTS

Detailed description of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

A portable urinary drain bag apparatus utilizing wireless remote control technology, in accordance with the present invention, turning first to FIG. 1, there is shown a suitable remote control transmitter device as shown in element 1, comprising "on" and "off" switch capability as shown in elements 18 & 19, that when the button is pushed to the "on" position as shown in element 18, a signal is sent to a wireless receiver relay as shown in element 2, which then transfers power from a rechargeable battery as shown in element 7, comprising of a battery connector as shown in element 6, connected through a battery connector as shown in element 17, wired to a commonly used terminal board as shown in element 5, which through a negative common connection as shown in element 15, a positive input connection as shown in element 14, and a positive output connection as shown in element 16, transferring power to a solenoid operated pinch valve, as shown in element 9.

In accordance with th important feature of my invention, the remote transmitter shown in element 1, when activated "on" sends a signal to the receiver relay shown in element 2, and through its connection to the terminal board as shown in element 3, opens the solenoid pinch valve as shown in element 9, releasing its pinched position on a flexible tube, as shown in element 10, which is connected to an outlet in a common urine drain bag, as shown in element 8. When the wireless remote transmitter as shown in element 1, is pushed to the "off" position as shown in element 19, a signal is sent to the wireless receiver relay as shown in element 2, which then de-energizes the relay, disconnecting the battery as shown in element 7, returning the solenoid pinch valve as shown in element 9, to its pinched, normally closed position on the flexible tube as shown in element 10, stopping the emptying of the bag as shown in element 8, allowing the bag to refill. If the operator fails to push the "off" button as shown in element 19, the wireless receiver relay de-energizes the solenoid returning it to its normally closed position. The circuit is protected by a fuse as shown in element 12. The battery can be recharged by connecting a suitable battery charger to a connector as shown in element 11. If the apparatus is used in a fixed location for an extended period of time, a suitable step down battery eliminator can be used by connecting at the battery connector as shown in element 17, in lieu of the battery as shown in element 7. The connected apparatus can be fitted together in a wearable pouch, vest or otherwise suited to the wearer for ease of movement and discreet appearance.

What is claimed is:

1. An apparatus to empty a urinary drain bag using wireless remote control technology comprising:
   a wireless remote transmitter;
   a receiver relay;
   a circuit board;
   a rechargeable battery;
   a battery charger connector;
   a soft shell connector;
   a solenoid operated pinch valve;
   a maintenance free flexible tube.

* * * * *

UNITED STATES PATENT AND TRADEMARK OFFICE
CERTIFICATE OF CORRECTION

PATENT NO. : 6,945,965 B2
DATED : September 20, 2005
INVENTOR(S) : Howard Anthony Whiting It is certified that error appears in the above-identified patent and that said Letters Patent is hereby corrected as shown below:

Column 1,
Lines 51-53, delete the paragraph.
Lines 59-64, delete the paragraph.

Column 2,
Lines 37-41, delete the paragraph.

Column 2, line 65 - Column 3, line 11,
Replace the text with the following two paragarphs:

Further, hard-wired mechanisms limit the mobility of the user to the location where the mechanism is mounted, usually to a wheelchair motor battery, limiting its operation only to the wheelchair or a fixed location. These mechanisms are often cumbersome and difficult to maintain. They cannot be operated at a distance by an attendant, requiring the attendant to manually operate the mechanism specifically at its location.

The invention does not control or affect bladder function but provides an external means for emptying a leg bag of urine content via a flexible tube using remote controlled technology. Further, the invention is portable and can be worn inconspicuously by the user for ease of mobility.

Column 3,
Line 22, delete "21. Tube from the catheter".

Column 4,
Line 35, replace with the following:

1. A portable apparatus for draining a bladder comprising:
a urinary drain bag (8);
a manually operated wireless remote transmitter (1) having "on" and "off" switch capability (18, 19);
a wireless remote controlled receiver relay (2) having a connector (3) operatively connected to a solenoid operated pinch valve (9) through a terminal board (5) and a second connector (20);
said terminal board (5) being protected by a fuse (12);
said terminal board (5) having a battery charger connector (11);
a rechargeable battery (7) having a battery connector (6) operatively connected to a second battery connector (17) on said terminal board (5), said terminal board (5) transferring power from the rechargeable battery (7) to the pinch valve (9);

UNITED STATES PATENT AND TRADEMARK OFFICE
CERTIFICATE OF CORRECTION

PATENT NO. : 6,945,965 B2
DATED : September 20, 2005
INVENTOR(S) : Howard Anthony Whiting It is certified that error appears in the above-identified patent and that said Letters Patent is hereby corrected as shown below:

<u>Column 4 (cont'd),</u> said pinch valve (9) having a pinched, normally closed position on said flexible tube (10), said flexible tube (10) being operatively connected to an outlet on the urinary drain bag (8);
wherein, manual activation of said "on" switch capability (18) of said remote transmitter (1) sends a wireless signal to said receiver relay (2) which in turn sends a signal through said terminal board (5) to the pinch valve (9) causing the pinch valve (9) to release its pinched position on the flexible tube (10) which allows liquid from said outlet in said urinary bag (8) to pass through said flexible tube (10) so as to drain said urinary bag (8);
further wherein, manual activation of said "off" switch capability (19) of said remote transmitter (1) sends a wireless signal to said receiver relay (2) which de-energizes the receiver relay (2) which disconnects said rechargeable battery from said pinch valve (9) causing the pinch valve (9) to return its pinched position on the flexible tube (10) which stops liquid in the urinary bag (8) from emptying through said flexible tube (10).

Signed and Sealed this

Seventh Day of February, 2006

JON W. DUDAS
*Director of the United States Patent and Trademark Office*